United States Patent [19]

Parker et al.

[11] 4,447,667

[45] May 8, 1984

[54] PROCESS FOR THE DEHALOGENATION OF ORGANIC COMPOUNDS

[75] Inventors: Dane K. Parker, Massillon; Timothy A. Sabo, Southington, both of Ohio

[73] Assignee: The Goodyear Tire & Rubber Company, Akron, Ohio

[21] Appl. No.: 421,678

[22] Filed: Sep. 22, 1982

[51] Int. Cl.$^3$ .......................... C07C 1/20; C10G 21/16

[52] U.S. Cl. ...................................... 585/469; 208/262

[58] Field of Search .......................... 585/469; 208/262

[56] References Cited

U.S. PATENT DOCUMENTS 4,340,471 7/1982 Jordon ................................ 210/101

*Primary Examiner*—Curtis R. Davis

*Attorney, Agent, or Firm*—D. O. Nickey

[57] ABSTRACT

There is disclosed an improved process for the destruction of halogenated organic compounds through treatment with an alkali metal aromatic radical anion reagent wherein the improvement comprises the elimination of the water quench step.

4 Claims, No Drawings

PROCESS FOR THE DEHALOGENATION OF ORGANIC COMPOUNDS

The present invention is related to and is an improvement on the process described in U.S. Pat. No. 4,284,516.

TECHNICAL FIELD

This invention is concerned with an improved process for dehalogenating organic compounds through treatment with an alkali metal aromatic radical anion reagent. In particular, this invention is directed to an improved method for quenching the excess reagent subsequent to dehalogenation of the organic compound.

BACKGROUND OF THE INVENTION

Many halogenated compounds are employed for a variety of practical uses, for example, as pesticides, soil fumigants, solvents, etc. It is known that a number of such compounds, particularly polyhalogenated compounds are toxic to plant and animal life. Although some of the compounds are bio and/or photodegradable (so they soon disappear from the environment) a substantial number are resistant to environmental degradation and remain in poisonous forms for many years. At present there are numerous processes available that will degrade such compounds into environmentally safe products.

Recent articles describing processes for the dehalogenation of organic materials, more specifically, for the destruction of polychlorinated biphenyls are *Science News,* Vol. 116, Nos. 25 and 26, page 422 (December 1979) and *Electronic and Engineering Times,* Oct. 29, 1979, pages 1 through 4.

U.S. Pat. No. 4,284,516 discloses and claims a process for the dehalogenation of low level concentrations (ppm-parts per million) of polychlorinated biphenyls (PCB's) dispersed within a contaminated substrate wherein said contaminated substrate is contacted with a reagent at a molar ratio of 25 to 500 moles of reagent per mole of halide contaminant contained within the fluid substrate; said reagent being prepared by:

(1) dispersing molten alkali metal selected from the group consisting of lithium, sodium and potassium at a temperature of at least 150° C. in the contaminated substrate that is inert toward the alkali metal and has a boiling point above the melting point of the alkali metal in the ratio of 250 millimeters of contaminated substrate per mole of alkali metal; (2) cooling the dispersed molten alkali metal/contaminated inert fluid mixture to ambient temperature with vigorous agitation under an inert atmosphere; (3) adding 1.3 moles of an aromatic radical anion forming compound selected from the group consisting of biphenyls, alkyl substituted biphenyls, napthalene, alkyl substituted naphthalene, anthracene, alkyl substituted anthracene, naphthacene, alkyl substituted naphthacene, ortho, meta and para terphenyl, and alkyl substituted terphenyls dissolved in a nonhydroxylic ether containing solvent with stirring.

The process of U.S. Pat. No. 4,284,516 provides effective dehalogenation through treatment with an alkali metal aromatic radical anion reagent wherein the reagent is prepared by disbursing molten alkali metal in an inert fluid. The specifics of reagent preparation and molar treatment ratios are discussed in detail in the U.S. Pat. No. 4,284,516 patent. Said U.S. Pat. No. 4,284,516 is herein incorporated by reference and made a part hereof.

The examples and discussion of U.S. Pat. No. 4,284,516 teach the quenching of the excess reagent, specifically sodium naphthalide, with an excess of water. The water is removed and the solvent is dried by evaporation under vacuum. The process of the present invention is specifically directed to an improvement on the U.S. Pat. No. 4,284,516 patent in that the difficulties and disadvantages associated with a water quench of the alkali metal aromatic radical anion reagent are overcome by utilizing carbon dioxide ($CO_2$) as the excess reagent quenching material.

The chemical reaction disclosed in U.S. Pat. No. 4,284,615 or for that matter any chemical reaction involving alkali metals has the potential to be hazardous even when conducted by qualified and experienced personnel. Extreme caution should be taken in this or any similar reaction involving organoalkali metal compounds, specifically organosodium compounds. Rapid generation of hydrogen is to be expected if sodium is contacted with water. For this reason utilization of U.S. Pat. No. 4,284,516 requires that adequate precautions be taken to assure that no metallic sodium enter the treatment vessel and that the water quench step be conducted in such a way as to avoid any possible explosive hazard.

The water quench, according to U.S. Pat. No. 4,284,516, should be added in small amounts, over a lengthy period of time, to control the rate of hydrogen release. Nitrogen or a similar inert gas should be used as a blanket to prevent the formation of potentially explosive hydrogen/oxygen mixtures.

U.S. Pat. No. 4,326,090 is very similar to U.S. Pat. No. 4,284,516, except that U.S. Pat. No. 4,326,090 teaches and claims the use of sodium naphthalide in the presence of sodium metal. The U.S. Pat. No. 4,326,090 disclosure does not suggest how the excess reagent is neutralized, but only says the process can be continuous with makeup quantities of naphthalene, solvent and sodium being added. It is evident that the process described in U.S. Pat. No. 4,326,090 or any dehalogenation process using alkali metals, would benefit from the improvement described in the instant invention.

As evidenced by the numerous corporations utilizing the process of U.S. Pat. No. 4,284,516 and the processes success in destroying highly stable PCB's, any improvement that would not generate an aqueous waste stream is desirable. Also, any improvement in the area of material recovery would also be desirable. The process of this invention allows for a nondistillative way for partial removal of the naphthalene from the bulk oil phase before or during processing. The prior art does not suggest or disclose the benefits that are attained through the use of the present invention.

DISCLOSURE OF THE INVENTION

There is disclosed an improved process for the dehalogenation of halogenated organic materials wherein the dehalogenation is accomplished through reaction with an alkali metal aromatic radical anion reagent, the improvement comprises, the quenching of the excess reagent after dehalogenation is completed by contacting the reaction mixture with carbon dioxide.

Even though U.S. Pat. No. 4,284,516 is directed to the effective dehalogenation of low level concentrations of halogenated organic compounds, the process of the present invention would be applicable to any reaction involving the dehalogenation of an organic material through the use of an alkali metal aromatic radical anion reagent. Further, the present invention would be useful in the process described in U.S. Pat. No. 4,326,090 where sodium metal is also present.

There is also disclosed a process of dehalogenating a polyhalogenated organic material wherein said polyhalogenated organic material is contacted with sodium naphthalide in the presence of sodium metal, the improvement comprises contacting the mixture with sufficient $CO_2$ to quench the excess reagent.

Representative of the halogenated compounds that can be dehalogenated through utilization of the process of the present invention are kepone (and its gemdiol); decachloropentacyclo($5.3.0.0^{2,6}.0^{3,9}.0^{4,8}$) decane-5-one; halogenated biphenyls; halogenated cyclodienes; such as aldrin, dieldrin, and hexachlorocyclopentadienes, dibromochloropropane, tetrachlorodibenzodioxin.

Representative of the alkalki metal aromatic radical anion reagents that can be employed in this process of this invention are lithium naphthalide, potassium naphthalide, sodium naphthalide, lithium anthracide, potassium anthracide and sodium anthracide. A more complete listing of the alkali metal aromatic radical anion reagents that can be quenched by the process of this invention can be found in Radical Anions by E. T. Kaisen and L. Kevan, Editors, Interscience Publishers, (1968). See also M. B. Scott, F. W. Walker, and V. L. Hansley, *Journal of the American Chemical Society*, 58, 2442 (1936), which are incorporated herein.

MORE DETAILED DESCRIPTION

The preparation of alkali metal aromatic radical anion reagents is known in the art, however, the advantages that can be obtained through quenching excess reagent with carbon dioxide instead of $H_2O$ are not disclosed. The following example is supplied to illustrate and not to limit the scope of the present invention.

EXAMPLE 400 grams of clean mineral oil dielectric fluid was charged to a 1000 milliliter round bottom flask. 150 grams of sodium naphthalide reagent, that had been previously prepared according to U.S. Pat. No. 4,284,516 was added to the round bottom flask. The sodium naphthalide reagent was prepared in tetrahydrofuran (THF) and mineral oil and contained 17.8 percent sodium naphthalide by weight. Carbon dioxide was generated by sublimation of dry ice in a filtration flask and bubbled through the oil via a glass dip tube. This treatment was made under vigorous agitation over a period of twenty minutes at room temperature. After the first two to three minutes of reaction the color of the oil began to change from the characteristic greenish-black color of the sodium naphthalide reagent to an orange-tan color, thus, signifying the reaction of the sodium naphthalide with carbon dioxide. Addition of a small amount of water to a sample of the oil produced no further reaction or color change, thus indicating all excess reagent had been quenched. The oil was then filtered over a quarter inch bed of diatomaceous earth and an waxy orange precipitate was recovered. The filtered oil was clear with a slight yellow color.

To those skilled in chemical engineering it would be evident that numerous means of contacting carbon dioxide with the reagent are possible. In fact, the addition of dry ice to the reaction mixture would be suitable and pressures above atmospheric can be advantageous in speeding the quench process. A sparge of gaseous carbon dioxide would be possible along with other known means of introducing a gaseous material to a liquid reaction mixture. The rate of carbon dioxide addition is not critical. The amount of carbon dioxide added to the reaction mixture will depend upon the concentration of the alkali metal reagent, however, as indicated from the Example a simple visual determination of color change is appropriate to determine when further addition of $CO_2$ would be unnecessary.

It has been found that the process of the present invention is a major process improvement that increases process safety and reduces overall cycle time and cost.

The process described in U.S. Pat. No. 4,284,516 as discussed earlier called for the slow addition of water to the treated oil after PCB destruction to neutralize the unreacted sodium naphthalide. This reaction forms sodium hydroxide and naphthalene with the evolution of hydrogen gas. The tetrahydrofuran was then recovered as a THF-water azeotrope which required further processing to dry the THF for recycle. Removal of naphthalene from the treated oil was also achieved by distillation before the oil could be returned to service.

The inherent hazards of employing water as a quenching agent in a system containing an alkali metal based compound are minimized through careful preparation and certification of the reagent and through meticulous control of the quenching operation. Maintenance of an inert atmosphere in the treatment vessel during the evolution of hydrogen is required to minimize the explosion hazard.

The process of the present invention substitutes carbon dioxide for the water as the quenching medium and it must be pointed out that this process change, only involves phases of the process after the detoxification of the PCB's and in no way affects the chemistry or efficiency of the PCB destruction reaction.

According to the present invention after a batch of treated oil has been certified as completely detoxifified, a stream of carbon dioxide is passed through the treated oil with agitation. The carbon dioxide reacts readily with the excess sodium naphthalide; forming naphthalene, sodium carbonate and a mixture of the disodium salts of Δ-dialin 3,4 or (1,4) dicarboxylic acid. No hydrogen gas is involved and at no time does water enter the system. THF can then be recovered in a pure dry form, by distillation of the quenched mixture either before or after filtration to remove insoluble by-products.

More specifically, after detoxification of the PCB contaminated dielectric fluid the treated oil was pumped from the treatment reactor to a separate quench reactor. The unreacted sodium naphthalide is then easily deactivated by sparging carbon dioxide through a dip-tube extending to the bottom of the reactor. Approximately 3.05 kilograms of $CO_2$ per kilogram unreacted sodium naphthalide is charged over a period of 15 minutes. The reactor was maintained at 10 psig during the quench operation to increase the solubility of $CO_2$ in the oil. This is achieved through the use of a control valve in the reactor vent line. The unreacted sodium naphthalide is converted to naphthalene, sodium carbonate, and a carboxylated residue. No hydrogen gas is evolved.

When the quench is complete the reactor pressure was slowly decreased to atmospheric which liberates additional dissolved $CO_2$. The oil is then ready for filtration. The following Table sets out the material balance for $CO_2$ quench. The data was obtained from three runs which were similar to the Example set out above.

TABLE I

| Material | Reactants (Kgs) | Products (Kgs) |
|---|---|---|
| Sodium Naphthalide | 2.2 | — |
| Carbon Dioxide | 3.85 | 2.6 |
| Naphthalene | — | 1.6 |
| Sodium Carbonate | — | .66 |
| Carboxylated Salts | — | 1.2 |
| TOTAL | 6.05 | 6.06 |

INDUSTRIAL APPLICABILITY

The process of the present invention has many advantages over the processes previously described. The exclusion of water from the process allows for the recovery of THF in pure, dry form eliminating additional process steps, does not generate a waste water stream for disposal, and improves overall process safety. Further, the process of the present invention reduces the total amount of naphthalene that must be removed from a treated oil before returning the oil to service. In some cases no further distillation of naphthalene will be required. The cost of THF and naphthalene recovery is significantly reduced and the overall cycle time for treating and finishing a batch of contaminated oil is reduced by approximately ten percent.

The process of this invention produces solid residual products, i.e. $Na_2CO_3$, carboxylated salts and polyphenylene polymer. Further, the process of this invention avoids foaming problems that had been encountered in using the $H_2O$ quench. As would be readily apparent to a chemical engineer, this process improvement will greatly aid in the engineering design of a commercial halogenated organic destruction process.

While certain representative embodiments and details have been shown for the purpose of illustrating the invention, it will be apparent to those skilled in this art that various changes and modifications may be made therein without departing from the scope of the invention.

What is claimed is:

1. A process for the dehalogenation of halogenated organic materials wherein the dehalogenation is accomplished through reaction with an alkali metal aromatic radical anion reagent, the improvement comprises quenching the excess reagent after dehalogenation is completed by contacting the reaction mixture with carbon dioxide.

2. A process of dehalogenating a polyhalogenated organic material wherein said polyhalogenated organic material is contacted with sodium naphthalide, the improvement comprises contacting the mixture with sufficient $CO_2$ to quench the excess reagent.

3. The process of claim 1 or 2 wherein said halogenated organic material is polychlorinated biphenyl.

4. A process according to claim 1 wherein said reagent is sodium napthalide.

* * * * *